United States Patent [19]

Katona

[11] Patent Number: 4,924,858

[45] Date of Patent: May 15, 1990

[54] ELECTROMAGNETIC SHOCKWAVE GENERATOR TRANSDUCER

[75] Inventor: Josef Katona, Kreuzlingen, Switzerland

[73] Assignee: Dornier Medizintechnik GMBH, Friedrichshafen, Fed. Rep. of Germany

[21] Appl. No.: 286,965

[22] Filed: Dec. 19, 1988

[30] Foreign Application Priority Data

Dec. 23, 1987 [DE] Fed. Rep. of Germany ....... 3743822

[51] Int. Cl.[5] ............................................ A61B 17/22

[52] U.S. Cl. ................................ 128/24 A; 606/128; 367/175

[58] Field of Search ................. 128/328, 24 A; 73/12, 73/668, 632, 642, 578, 591; 367/142, 174, 175, 182; 181/139, 142, 143-143; 381/150, 151

[56] References Cited

U.S. PATENT DOCUMENTS

| | | | |
|---|---|---|---|
| 4,697,588 | 10/1987 | Reichen | 128/328 S |
| 4,793,329 | 12/1988 | Mahler et al. | 367/175 |
| 4,794,914 | 1/1989 | Mahler et al. | 367/175 |
| 4,796,608 | 1/1989 | Koehler | 128/328 S |

FOREIGN PATENT DOCUMENTS

| | | | |
|---|---|---|---|
| 3505894 | 8/1986 | Fed. Rep. of Germany | 128/328 S |

*Primary Examiner*—Max Hindenburg
*Assistant Examiner*—Robin R. Longo
*Attorney, Agent, or Firm*—Ralf H. Siegemund

[57] ABSTRACT

A transducer to be used in a shock wave generator including a support, at least one energizing coil mounted on the support; at least one, preferably two copper or silver membranes are placed on the coil and insulated from each other; an outer, stainless steel membrane is grounded and an electrical insulation is interposed between the first and the second membranes.

6 Claims, 1 Drawing Sheet

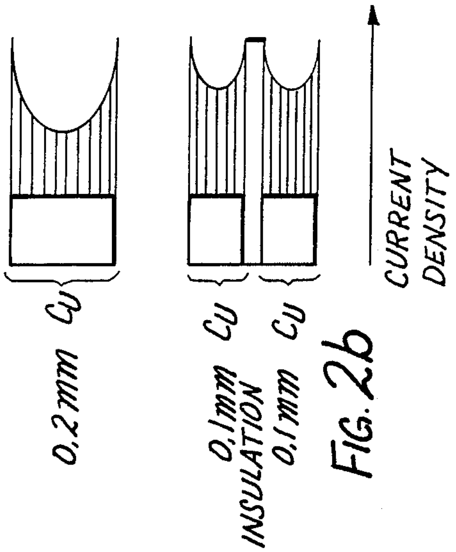
FIG. 2a
FIG. 2b
FIG. 1
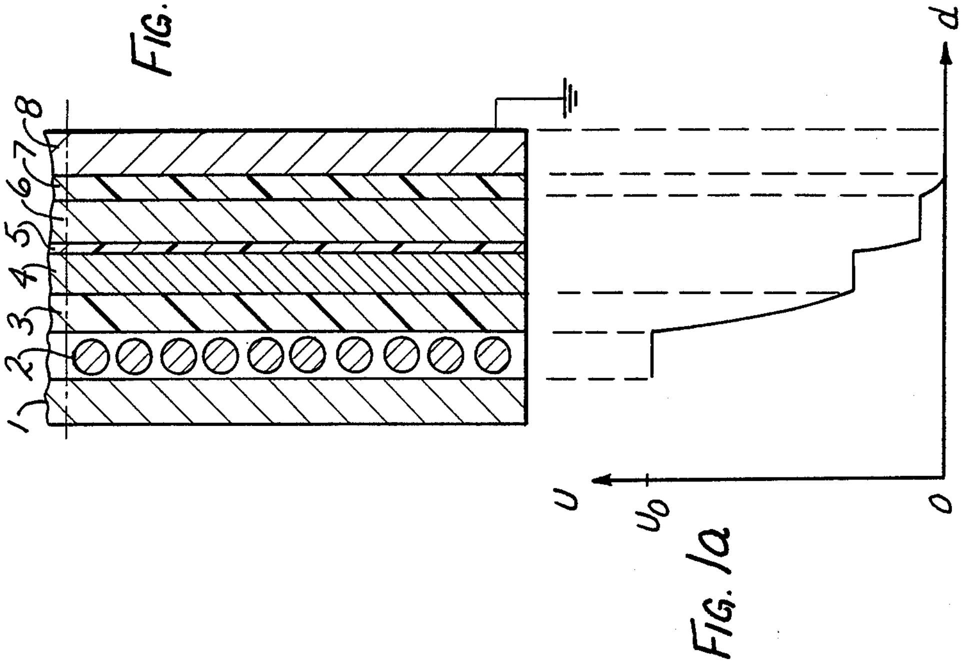
FIG. 1a

ELECTROMAGNETIC SHOCKWAVE GENERATOR TRANSDUCER

BACKGROUND OF THE INVENTION

The present invention relates to a transducer to be used in a shock wave generator; the transducer broadly being comprised of some kind of base support, a metal membrane, some form of electrical insulation and an energizing coil by means of which the membrane is set into vibratory motion for purposes of generating a shock wave assuming a proper stimulating pulse is applied.

Electromagnetically generated shock waves are used in the important field of comminution of concrements in the body of living beings. German printed patent 33 28 066 discloses a generator of this kind. Also the journal "Akustische Beihefte", (Acoustic Miscels or Supplements) 1962, Volume 1, pages 158–202, describes a so called shock wave tube. Herein a flat coil is provided and a copper membrane is energized by that coil but separated therefrom physically through an insulation foil. A water filled tube adjoins the copper membrane. As a voltage is applied to the coil having a value of 2 to 20 kV, a magnetic field as induced by current flow in the copper membrane establishes repelling forces causing the membrane to recede from i.e. to be forced away from the coil. This way one provides for a planar pressure pulse, basically over the extension of the membrane width of pulse which is so to speak converted by and in the water into a steep shockwave front to be available for one purpose or another at the end of the tube. Shock wave tubes of this kind are used e.g. in chemistry for purposes of providing certain investigations.

DESCRIPTION OF THE INVENTION

It is an object of the present invention to provide a new and improved transducer to be used in a shock wave generator for a specific purpose outlined above but beginning with the prior art configuration as stated.

In accordance with the preferred embodiment of the present invention, it is suggested to provide a plurality of metal membranes which are at least separated from each other through insulation so that in relation to an energizing coil there are at least two layers of insulation provided for separating the coil from the membranes and the membranes themselves and each other. An outer membrane is a relatively poor conductor but strong, e.g. made of stainless steel and is electrically grounded. One or more inner membranes are good conductors, they are preferably made of copper or silver. The potential of these high conductor membranes is more or less floating on account of insulative separation.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a cross section through a transducer constructed in accordance with the preferred embodiment of the present invention for practicing the best mode thereof;

FIG. 1*a* is a voltage diagram plotting potential levels as they occur in the transducer structure shown in FIG. 1; the diagram being in terms of thickness values d through the generator and is drawn in alignment with the various elements of FIG. 1; and FIG. 2 illustrates in various portions (a and b) the exemplary current densities in membranes as they may occur and are being or could be used in the construction shown in FIG. 1.

Proceeding now to the detailed description of the drawings FIG. 1 illustrates as shown a transducer to be used in a shock wave generator which is comprised of a basic body and element 1 having primarily the function of supporting. Immediately supported on the body 1 is a coil 2 of the suitable configuration. The turns of the coil are separated; the coil as a whole is covered by an electric insulation 3. Adjoining the insulation layer 3 is a first membrane being a copper membrane 4 and being separated through another, relatively thin insulation foil 5 from a second copper membrane 6. A somewhat thicker, electrically insulating layer 7 is provided on top of the second copper member 6, and this foil 7 in turn carries a stainless steel membrane 8 being grounded as schematically indicated.

It can thus be seen that this specific example shows two metal foils, namely 4 and 6 which are relatively speaking made of very good electrically conductive material. One could provide more membrane if that is desirable and they could be made of silver. The outer electrode 8 is strong and not as good a conductor. Preferably one uses stainless steel.

The various layers shown are physically interconnected in a conventional fashion through bonding by means of adhesive. The FIG. 1 illustrates this transducer on a very enlarged scale. A realistic value is e.g. a total thickness from say the outer surface of insulator 3, through the various membrane layers to be roughly about 1 mm. By way of example one can use the following values. The copper membranes each are from 0.05 to 0.2 mm thickness. As stated the Cu membranes could be replaced by silver of comparable dimension. The insulation foil 7 should be between 0.025 and 0.125 mm and the stainless steel membrane 8 should be between 0.1 and 0.2 mm. It can readily be seen that the total thickness will not exceed 1 mm.

As a voltage $U_o$ is applied to the coil 2, the potential distribution is as shown in FIG. 1*a* and the zero level presents the fact of grounding; the stainless steel membrane 8 being connected to assume ground potential. The Cu membranes 4 and 6 are at more or less slowing potentials, in between the $U_o$ level and the level 0 whereby owing to their good conductivity there is practically no potential drop across the thickness of each of the two copper membranes.

FIG. 2 illustrates in line a, the current density distribution for a simple copper membrane of 0.2 mm thickness. FIG. 2*b* illustrates the current density in two copper membranes each being 0.1 mm thick and being separated by an electrical insulation layer that is thinner than 1/10 mm. Owing to the skin effect the current density at high frequencies is not uniformly distributed across the conductor cross section. Maximum penetration depth for the frequency used is about 0.2 mm. Please note that the voltage applied to the coil 2 is a pulse with steep flanks thus being rich in high frequences.

The distribution of the current density is schematically shown in FIG. 2. As can be seen the integral of the current density across the respective membrane is larger if two membranes rather than one are used. This increases the efficiency for given voltage level of operation. The repulsion forces exerted upon the membrane and, therefore, the amplitude of the resulting pressure and shock wave pulse are larger. In the case of a good conducting membrane (copper, silver) with a thickness larger than 0.4 mm the current density actually drops to zero in the interior. This is not the case when the membrane is laminated. The distribution of the current density is similar.

The invention offers the following advantages. There is a reduction in loss of efficiency owing to the fact that it is not the copper membranes (4, 6) which are grounded. What is grounded is the outer membrane 8 which is relatively poor conductor and in that sense does not participate in a loss producing fashion. The heating of the system is, therefore, reduced owing to the increase in efficiency (and vice versa). The skin effect is not any more a limiting factor concerning the total thickness of the membrane, being a good conductor as stated and which was demonstrated above with a reference to FIG. 2. One can, therefore, and should use several membranes in a stack arrangement with a total thickness of course larger than the thickness of each individual membrane.

The potential distribution between the coil on one hand and the grounded outer membrane on the other hand is more favorable as shown in FIG. 1*a* because the membranes in between are electrically insulated vis-a-vis the outer membrane 8. Therefore as a high voltage is applied to the coil, two membranes 4 and 6 and others if they are provided assume a definitely lower potential level. This was found to increase the use life of the membrane and of the system as a whole.

The use life of such a transducer is generally determined by the breakthrough strength of insulation between e.g. the coil 2 and any of the membranes. Owing to the more favorable potential distribution in this multiple membrane systems, each of the insulation layers are not subjected anymore to such a strong electrical potential and that means its use life increases.

The membranes 4 and 6 i.e. in this case one of the membranes could actually be placed directly on the coil provided there is adequate electrical insulation between the outer membrane 8 and the rest of the system. In the illustrated case, however, it is the insulation layer 3 that provides the main insulative separation between coil 2 and grounded membrane 8. Distributing the insulation improves also the coupling, in an electric sense of the membrane in the coil since any stray field is minimized. From an overall point of view it was found that the eddy current losses are lower than in the conventional transducers.

The invention is not limited to the embodiments described above but all changes and modifications thereof, not constituting departures from the spirit and scope of the invention, are intended to be included.

What is claimed:

1. For use in a shock wave generator, a transducer comprising:
   - a base support;
   - at least one energizing coil mounted on said base;
   - at least one first, electrically good conducting membrane on the coil;
   - an outer, grounded metal membrane of lesser conductivity; and
   - electrical insulation means interposed between the first and the second membrane.

2. A transducer as in claim 1 wherein said second membrane has a greater strength than the first membrane.

3. A transducer as in claim 2 said outer membrane being made of stainless steel.

4. A transducer as in claim 1 the first membrane being made of copper or silver.

5. A transducer as in claim 1 wherein said first membrane being made of copper from 0.05 to 0.2 mm thick, said insulation being between 0.025 to 0.125 mm thick and said second outer membrane being made of stainless steel having a thickness from 0.1 to 0.2 mm.

6. A transducer as in claim 1 there being a plurality of electrically insulated first membranes provided and disposed between said second electrode of relatively low conductivity and said coil.

* * * * *